United States Patent [19]
Kroll et al.

[11] Patent Number: 5,620,464
[45] Date of Patent: *Apr. 15, 1997

[54] SYSTEM AND METHOD FOR DELIVERING MULTIPLE CLOSELY SPACED DEFIBRILLATION PULSES

[75] Inventors: Mark W. Kroll, Minnetonka; Dennis A. Brumwell, Bloomington; Ann M. Donohoo, Shorview, all of Minn.

[73] Assignee: Angeion Corporation, Plymouth, Minn.

[*] Notice: The term of this patent shall not extend beyond the expiration date of Pat. No. 5,383,907.

[21] Appl. No.: 376,353

[22] Filed: Jan. 23, 1995

Related U.S. Application Data

[63] Continuation-in-part of Ser. No. 993,094, Dec. 18, 1992, Pat. No. 5,407,444, and a continuation-in-part of Ser. No. 993,292, Dec. 18, 1992, Pat. No. 5,383,907.

[51] Int. Cl.⁶ .................................................. A61N 1/39
[52] U.S. Cl. ............................................................. 607/5
[58] Field of Search ............................. 320/1; 307/106, 307/108–110, 46, 48; 607/4, 5, 7, 11, 12

[56] References Cited

U.S. PATENT DOCUMENTS

| | | | |
|---|---|---|---|
| 3,094,634 | 6/1963 | Rappaport . | |
| 3,211,154 | 10/1965 | Becker et al. | 607/5 |
| 3,740,273 | 6/1973 | Adler . | |
| 3,767,947 | 10/1973 | Adler et al. . | |
| 3,898,994 | 8/1975 | Kolenik et al. | 607/9 |
| 3,959,706 | 5/1976 | Mabuchi et al. | 320/3 |
| 4,002,497 | 1/1977 | Brown . | |
| 4,024,420 | 5/1977 | Anthony et al. . | |
| 4,025,860 | 5/1977 | Shibata et al. | 320/3 |
| 4,026,726 | 5/1977 | Carney . | |
| 4,504,773 | 3/1985 | Suzuki et al. | 607/5 |
| 4,530,550 | 7/1985 | Kondo | 320/1 |
| 4,628,143 | 12/1986 | Brotz . | |
| 4,637,397 | 1/1987 | Jones et al. | 607/5 |
| 4,708,145 | 11/1987 | Tacker, Jr. et al. . | |
| 4,736,150 | 4/1988 | Wagner | 320/21 |
| 4,821,723 | 4/1989 | Baker, Jr. et al. | 607/7 |
| 4,835,433 | 5/1989 | Brown . | |
| 4,931,947 | 6/1990 | Werth | 320/3 |
| 4,996,984 | 3/1991 | Sweeney . | |
| 5,000,579 | 3/1991 | Kumada et al. . | |
| 5,107,834 | 4/1992 | Idecker et al. . | |
| 5,199,429 | 4/1993 | Kroll et al. . | |
| 5,235,979 | 8/1993 | Adams | 607/5 |
| 5,306,291 | 4/1994 | Kroll et al. . | |
| 5,312,443 | 5/1994 | Adams et al. . | |
| 5,334,219 | 8/1994 | Kroll . | |
| 5,372,605 | 12/1994 | Adams et al. . | |
| 5,383,907 | 1/1995 | Kroll . | |
| 5,407,444 | 4/1995 | Kroll . | |
| 5,473,526 | 12/1995 | Svensson et al. | 307/109 |

FOREIGN PATENT DOCUMENTS

| | | | |
|---|---|---|---|
| 516405 | 6/1976 | U.S.S.R. | 607/5 |

OTHER PUBLICATIONS

Kugelberg, "Scandinavian Society of Thoracic Surgery", pp. 123–128, Oct., 1965.

Sweeney and Reid, II 610, Supplement II Circulation, vol 84, No. 4, Oct., 1991, No. 2425.

Johnson et al., NASPE Abstracts, Apr. 1991, Part II, No. 391, PACE, vol 14, p. 715.

*Primary Examiner*—William E. Kamm
*Assistant Examiner*—George R. Evanisko
*Attorney, Agent, or Firm*—Brad D. Pedersen

[57] ABSTRACT

A main energy delivery electrical circuit for use in an implantable cardioverter defibrillator device comprises a low power output primary defibrillator battery, a high power output intermediate power intensifying capacitor system, a switch for permitting the intermediate power intensifying capacitor system to rapidly charge a main energy delivery capacitor, and a main energy delivery capacitor. The main energy delivery capacitor is configured for discharging, in a first pulse, an electrical charge derived from the primary battery, and for discharging certain subsequent pulses of electrical charge derived from the intermediate power intensifying capacitor system. The circuit permits the implantable cardioverter defibrillator device to deliver multiple closely spaced defibrillation pulses to a heart.

18 Claims, 4 Drawing Sheets

SYSTEM AND METHOD FOR DELIVERING MULTIPLE CLOSELY SPACED DEFIBRILLATION PULSES

This application is a continuation-in-part application of two pending applications previously filed with the United States Patent and Trademark Office, both of which were filed on Dec. 18, 1992, the first of which was entitled "STAGED ENERGY CONCENTRATION FOR A DEFIBRILLATOR", Ser. No. 07/993,094, and the second of which was entitled "SYSTEM AND METHOD FOR DELIVERING CLOSELY SPACED DEFIBRILLATION PULSES", Ser. No. 07/993,292, U.S. Pat. No. 5,383,907 both of which are assigned to the assignee of the present invention, and each of which is hereby incorporated by reference in this application. This application is also related to a co-pending application filed concurrently herewith entitled "STAGED ENERGY CONCENTRATION FOR AN IMPLANTABLE BIOMEDICAL DEVICE", Ser. No. 08/Xxx,xxx, which is assigned to the assignee of the present invention and which is hereby incorporated by reference in this application.

FIELD OF THE INVENTION

A system and method is disclosed for delivering closely spaced multiple defibrillation pulses. More particularly, the amount of energy required in each pulse is low, which reduces the overall size of the main energy delivery capacitor required for pulse delivery. This also reduces the overall size of an implantable cardioverter defibrillator device utilizing the main energy delivery capacitor.

BACKGROUND OF THE INVENTION

Electrical defibrillation of the heart has been accomplished in a research and clinical setting for many years. Recently, implantable cardioverter defibrillators, known as ICDs, have been used to provide defibrillation pulses in these settings. The pulses may vary between monophasic and biphasic pulses. A multiple pulse technique was also developed for defibrillation which comprises a plurality of shorter duration pulses, possibly with a variety of spacing between the pulses. In all of the above methods, a minimum energy requirement exists which requires main energy delivery storage capacitors of certain size. Optimization of capacitor size of the main energy delivery capacitors, in combination with the advantages of the theoretically optimum multiple pulse technique is desirable.

Efforts to create improved power generation and distribution systems in multiple pulse defibrillation devices are demonstrated in many U.S. patents. However, considerable advances are necessary to reduce the level of intrusion which ICD devices create in the patient and to optimize the performance of these devices.

SUMMARY OF THE INVENTION

A main energy delivery electrical circuit for use in an implantable cardioverter defibrillator device comprises a low power output primary defibrillator battery, a high power output intermediate power intensifying capacitor system, a switch for permitting the intermediate power intensifying capacitor system to rapidly charge a main energy delivery capacitor, and a main energy delivery capacitor. The main energy delivery capacitor is configured for discharging, in a first pulse, an electrical charge derived from the primary battery and for discharging certain subsequent pulses of electrical charge derived from the intermediate power intensifying capacitor system. The circuit permits the implantable cardioverter defibrillator device to deliver multiple closely spaced defibrillation pulses to a heart.

A main energy delivery electrical circuit for use in an implantable cardioverter defibrillator comprises a low power output primary defibrillator battery, a high power output intermediate power intensifying capacitor system, a main energy delivery capacitor, and a charging sub-circuit. The main energy delivery capacitor is configured for discharging, in a first pulse, an electrical charge derived from the primary battery and for discharging certain subsequent pulses of electrical charge derived from the intermediate power intensifying capacitor system. The charging sub-circuit permits simultaneous charging from the low power output primary defibrillation battery to both the high power output intermediate power intensifying capacitor system and the main energy delivery capacitor.

A rapid pulse power system for use with an implantable cardioverter defibrillator is provided. The system permits rapid transition from a widely spaced defibrillation pulse sequence to a closely spaced defibrillation pulse sequence. The rapid pulse power system comprises a low power output primary defibrillator battery, a high power output intermediate power intensifying capacitor system, switch means for permitting the intermediate power intensifying battery to rapidly charge a main energy delivery capacitor, control means for responding to a remote signal and selectively discharging a main energy delivery capacitor, and a main energy delivery capacitor. The capacitor is configured for discharging, in a first pulse, an electrical charge derived from the primary battery and for discharging certain subsequent pulses of electrical current derived from the intermediate power intensifying capacitor system. The circuit permits the implantable cardioverter defibrillator device to deliver multiple closely spaced defibrillation pulses to a heart at any time interval following an initial defibrillation attempt.

DETAILED DESCRIPTION OF THE INVENTION

Figure 1:
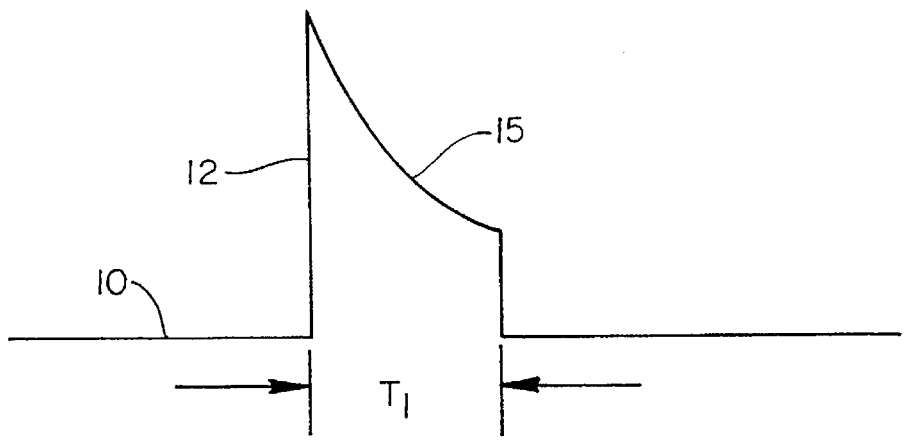
FIG. 1 is a representative monophasic waveform for an implantable cardioverter defibrillator.

FIG. 1 illustrates a common waveform utilized by implantable cardioverter defibrillators. Waveform 10 discloses the monophasic pulse portion 12 exhibited during capacitive discharge, Monophasic pulse 12 is derived by charging a large capacitor to high voltage and discharging that capacitor into the heart. After a period of time $T_1$ has elapsed, the current flow is removed which results in the truncated shape 15 of the monophasic pulse 12.

Figure 2:
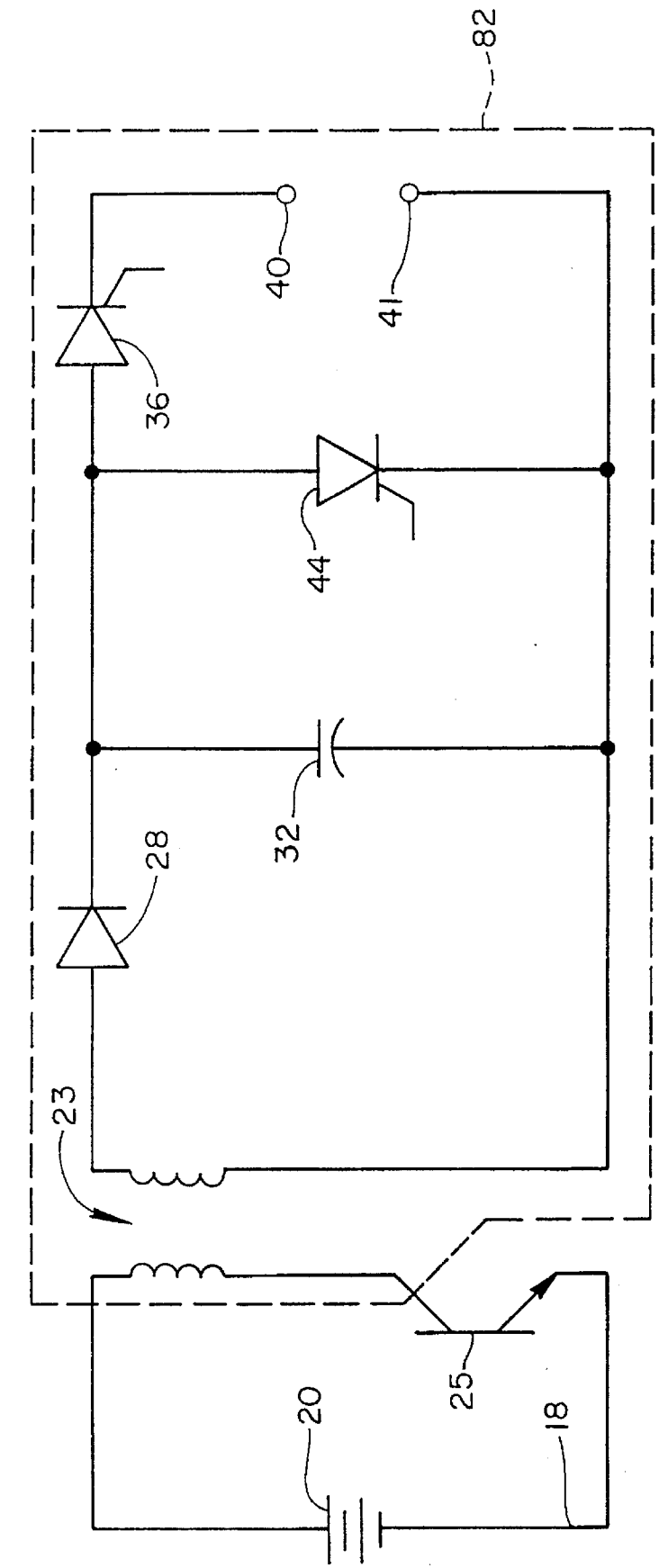
FIG. 2 is a schematic circuit diagram illustrating representative prior art circuitry for an implantable cardioverter defibrillator.

FIG. 2 illustrates representative circuitry for generating a pulse similar to that disclosed in FIG. 1. Circuit 18 comprises battery 20 which is used to provide a current through the primary winding of transformer 23. The current is cycled on and off at a high rate of speed by control system 30 using switching transistor 25. The output from transformer 23 is rectified by diode 28 and is captured in the main storage capacitor 32. In order to deliver the pulse to the heart, an inverter/output circuit 34 is used, depending upon whether a monophasic or biphasic output is desired. For a monophasic output, silicon controlled rectifier 36 is triggered by control system 30, thereby providing a current path from capacitor 32 to the electrodes 40, 41 in the heart. At the point of pulse truncation at the end of time period $T_1$, silicon controlled rectifier 44 is triggered. This quickly discharges capacitor 32 and back biases silicon controlled rectifier 36 to shut off the flow of current through electrodes 40, 41 to the heart. It will be appreciated that numerous variations to the monitoring, control and capacitor configurations of circuit 18 are known in the art and are equally possible with the present invention, as shown for example in U.S. Pat. Nos. 5,199,429, 5,306, 291, 5,312,443, 5,334,219 and 5,372,605.

Figure 3:
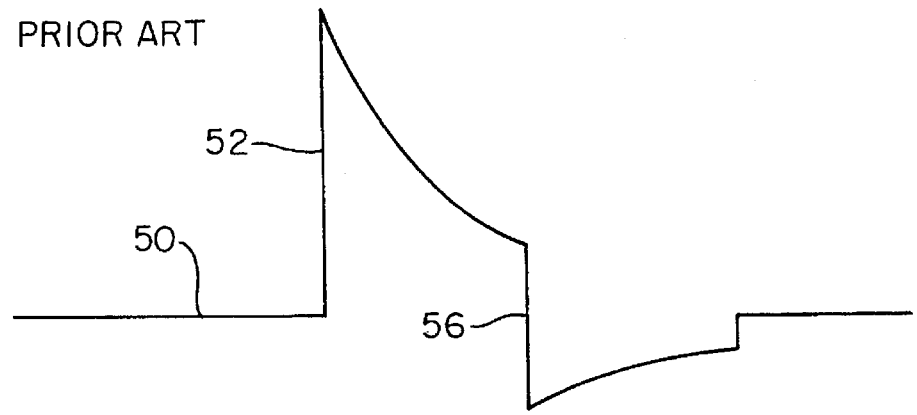
FIG. 3 is a representative biphasic waveform for an implantable cardioverter defibrillator.

The biphasic waveform 50 depicted in FIG. 3 is an improvement over the monophasic waveform 10 of FIG. 1. Biphasic pulse 52 commences with a first phase that is substantially identical to that of monophasic pulse 12. However, at the time of truncation following time period $T_1$ the current is not merely interrupted but is reversed, producing the configuration shown as pulse section 56. This reversal is commonly done by the use of current reversal means, such as H-bridge circuitry, for the inverter/output circuit 34. Use of a biphasic pulse technique may reduce the energy required for each defibrillation pulse by about an average of 25 percent.

The energy required to defibrillate in each pulse is a critical determinant of the size of an implantable cardioverter defibrillator. This is because the main storage capacitor, such as capacitor 32 shown in FIG. 2, is normally the largest single component in such an ICD device. The most efficient proven capacitors of this type will store about 1.5 Joules per cubic centimeter, and are also the major determinant of the volume of an implantable cardioverter defibrillator. Since this class of defibrillator device is implantable, it is critical that it be made as small as possible. This is particularly important as now ICD devices are designed for pectoral implantation. This directly translates into a severe constraint on the volume of the device and the energy available per defibrillation pulse.

Figure 4:
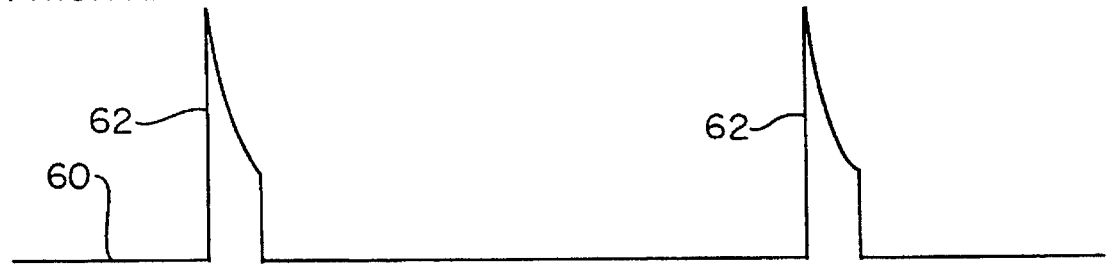
FIG. 4 is a conceptual multiple short pulse waveform for a defibrillator.

The multiple pulse defibrillation concept as generally shown in FIG. 4 has been experimented with for many years. Ventricular defibrillation of dogs with waves comprising two pulses with a pulse length and pulse interval adjusted so that those cells excitable at any moment are defibrillated by the first pulse and are refractory to the second pulse was disclosed by Kugelberg as early as October, 1965, in the Scandinavian Society of Thoracic Surgery, pages 123–128. Kugelberg considered a variety of pulses and spacings and found that defibrillation was indeed quite possible with multiple pulses. U.S. Pat. No. 4,996,984, issued to Sweeney, discloses adjusting the timing between multiple bursts of defibrillation energy based upon the fibrillation cycle length of the mammal. Similarly, Sweeney and Reid disclose that the interaction between multiple pulses is non-linearly related to the fibrillation cycle length, and that the spacing between multiple pulses may be a fixed percentage of the spacing between fibrillation zero crossings in the heart. (II-610, Supplement II Circulation, Vol. 84, No. 4, October, 1991, No. 2425). Johnson et al disclose that successive biphasic shocks delivered through two different electrodes may be either beneficial or detrimental depending on the delay between the two shocks. (NASPE Abstracts, April, 1991, Part II, no. 391; PACE, Vol. 14, p. 715). Other examples of multiple pulse defibrillation systems include U.S. Pat. Nos. 5,107,834 to Ideker et al and 4,708,145 to Tacker, Jr. et al.

In principal, the above disclosures demonstrate that the energy per pulse in a multiple or closely spaced pulse technique using different pathways, multiple defibrillators, or other inefficient means of energy generation and distribution, may be reduced from what is commonly used in a single or widely spaced pulse technique. These are considerable limitations and disadvantages in the field of implantable cardioverter defibrillators.

Current medically accepted practice requires a minimum amount of energy for implantable cardioverter defibrillators on the order of about 20–30 Joules. The multiple pulse waveform 60 of FIG. 4 depicts activation of a representative multiple defibrillator system. The system would likely lower the total defibrillation threshold by about 50 percent, cutting the 30 Joule accepted limit to about 15 Joules per pulse. However, such a system requires multiple sizeable main energy delivery capacitors. No disclosure exists for either a method or structure to achieve multiple closely spaced pulses using an intermediate power intensifier as disclosed below. The present invention teaches means for overcoming the impediments of the theoretical multiple pulse systems. The invention also discloses novel means for providing a rapid pulse power system for use with conventional ICD circuits to permit optional prompt transition from a widely spaced defibrillation pulse sequence to a closely spaced defibrillation pulse sequence.

The energy generation problem is appreciated more fully by calculating the charging power required of a representative main energy delivery capacitor system in an ICD device. Assuming a conventional single pulse defibrillator which is designed to deliver a 30 Joule pulse, a 10 second delay for capacitor charging is considered acceptable after fibrillation is detected. The charging power is described by simple calculation of 30 Joules divided by 10 seconds, which yields 3 watts. This 3 watt level of power is available from high quality defibrillation primary cells, such as lithium silver vanadium pentoxide cells, although others may be suitable.

Assuming a use of two closely spaced pulses 62, 63, as shown in waveform 60 of FIG. 4, defibrillation could occur with 15 Joules in each pulse. The main energy delivery capacitor could be designed to store only 15 Joules and could be made of only half the size of present capacitors. However, although the main energy delivery capacitor has 10 seconds to charge in order to create the first pulse 62 by use of present circuitry, the main energy delivery capacitor then must be quickly recharged to provide the second pulse 63. Generally, the amount of time required to quickly recharge is the same time as that required for optimum spacing between the two pulses, which is about 0.25 seconds. Therefore, the charging power must be equal to 15 Joules divided by 0.25 seconds. This requires a 60 watt power source. Currently, there is no functional implantable battery which is capable of providing such power output.

Figure 5:
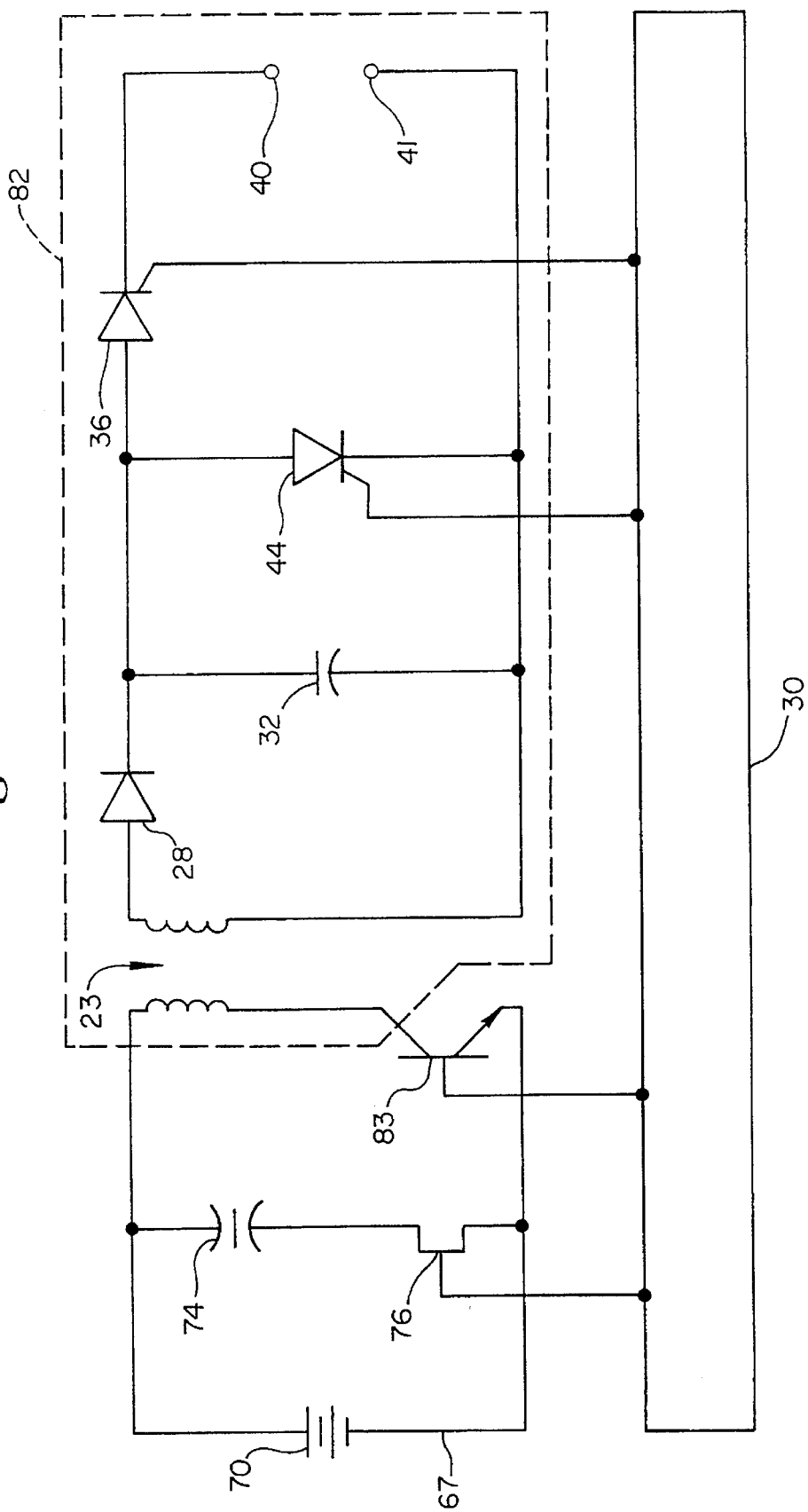
FIG. 5 is a schematic circuit diagram of one embodiment of the implantable cardioverter defibrillator rapid pulse circuitry of this invention.

FIG. 5 discloses the essential circuit elements of one embodiment of the present invention in which circuit 67 uses both a primary battery and an intermediate power intensifying capacitor system, with the latter comprising a very high power output capacitor system to provide the high charging power between capacitor pulses. As shown, battery 70 is a low amperage primary defibrillation cell, which is preferably a lithium silver vanadium pentoxide type, although other materials are feasible. When fibrillation is detected, battery 70 is used to quickly charge a intermediate power intensifying capacitor system 74 which is capable of very high power output. This is preferably accomplished through the use of transistor switch 76. Power intensifying capacitor system 74 is preferably selected from a list of possible high power, high energy density capacitors, such as dual layer capacitors. When power intensifying capacitor system 74 has been sufficiently charged then it is useful as a source of high current charging power to capacitor 32 in circuitry sub-section 82, shown in circuit 18 of FIG. 2 and in circuit 67 of FIG. 5.

Power intensifying capacitor system 74 is preferably comprised of one or more double layer capacitors having no permanent dielectric. Currently available capacitor technology is capable of producing a double layer capacitor with a maximum voltage rating of 11 volts and a maximum energy density of around 10.7 J/cc. Examples of such a double layer capacitor are the Panasonic SG and NEC FE capacitors. Other possible dual layer capacitors useful with the present invention include the Ruthenium Oxide (RO) dual layer capacitor developed by Pinnacle Research Co. New manufacturing technologies and materials are being introduced for double layer capacitors which have the potential to increase the capacitance and voltage ratings of these devices. These improvements involve new materials with increased surface areas (which directly relates to capacitance), and new manufacturing techniques to reduce the space between the plates which decreases both the overall resistance and the overall size of the power intensifying capacitor. Low impendence dual layer capacitors, for example, are the subject of intensive research and development in providing power supply systems for electrical cars and the advantages gained in that area could be applied to create a custom made optimized device for use in connection with the present invention.

In the case of the power intensifying capacitor system 74, the critical value of the dual layer capacitor system is the power transfer capability of the system. In order to deliver the second 10 J "half" of a total 20 J countershock, for example, power intensifying capacitor system 74 must be capable of transfering 13.3 J to the primary coil 21 of transformer 15 within less than 250 ms, assuming that the transformer has a 75% transfer efficiency. With these time and energy constraints, the power required of power intensifying capacitor system 74 is equal to:

$$P = E/t$$
$$= 13.3 \text{ J}/(250 \text{ ms})$$
$$= 54 \text{ W}$$

In addition, the time constant of of the power intensifying capacitor system 74 for maximum power transfer must be such the required energy is transferred to the primary coil 21 within a time constant $\tau=(RC)$ of less than 250 ms, where C is the effective capacitance of power intensifying capacitor system 74 and R is the equivalent series resistance (ESR) of power intensifying capacitor system 74. At present, applicants are not aware of any dual layer capacitors which would meet these specifications, however, existing commercially available dual layer capacitors, such as the NEC FE, are close to being within the range of meeting these specifications, and the development of newer, more efficient dual layer capacitors should make the present invention practical as well. The key is to have a low impedance dual layer capacitor with an ESR of less than about 0.25 Ω, as compared to existing high impedance dual layer capacitor systems with ESRs of greater than 0.5 Ω, and often greater than 10 Ω. The NEC FE dual layer capacitor, for example, has ratings of

| | | |
|---|---|---|
| Capacitance | = | 1.5 F |
| Voltage | = | 5.5 V |
| ESR | = | .6 Ω |
| Volume | = | 28.3 cc |
| Weight | = | 20 grams |
| $E_{std}$ | = | 22.5 J |
| P | = | 50.4 W |

A preferred dual layer capacitor system ideally suitable for use with the present invention, for example, would consist of a dual layer capacitor having ratings of:

| | | |
|---|---|---|
| Capacitance | = | 2 F |
| Voltage | = | 5.5 V |
| ESR | = | .1 Ω |
| Volume | = | 15 cc |
| Weight | = | 15 grams |
| $E_{std}$ | = | 30.25 J |
| P | = | 121 W |

The difference between the capacitor charging circuitry of FIG. 5 and FIG. 2 is an approximately 18:1 charging power ratio of 54 watts rather than 3 watts. The charging circuitry shown as schematic circuit 67 provides power means for recharging the capacitor of the related ICD device, after an initial discharge, between subsequent multiple pulses. This eliminates the need for additional main energy delivery capacitors and eliminates about half of the capacitor volume of known ICD devices. The invention also results in significant improvement in size and operation of an ICD device.

Preferably, the present invention is capable of charging capacitor system 32 within 5 seconds. Optimally, the power intensifying capacitor system 74 and the primary defibrillation battery 70 are arranged such that the capacitor system 32 can be charged in a time interval which is within the range of greater than 10 ms and less than 1 s between pulses.

An alternate embodiment for charging power intensifying capacitor system 74 after fibrillation is detected comprises maintaining power intensifying capacitor system 74 substantially charged at all times. This may be accomplished by a variety of methods, including using primary battery 70 to provide a continuous nominal charge to power intensifying capacitor system 74, which is a recharging technique similar to that disclosed in previously identified co-pending U.S. patent application entitled "STAGED ENERGY CONCENTRATION FOR AN IMPLANTABLE BIOMEDICAL DEVICE".

Figure 6:
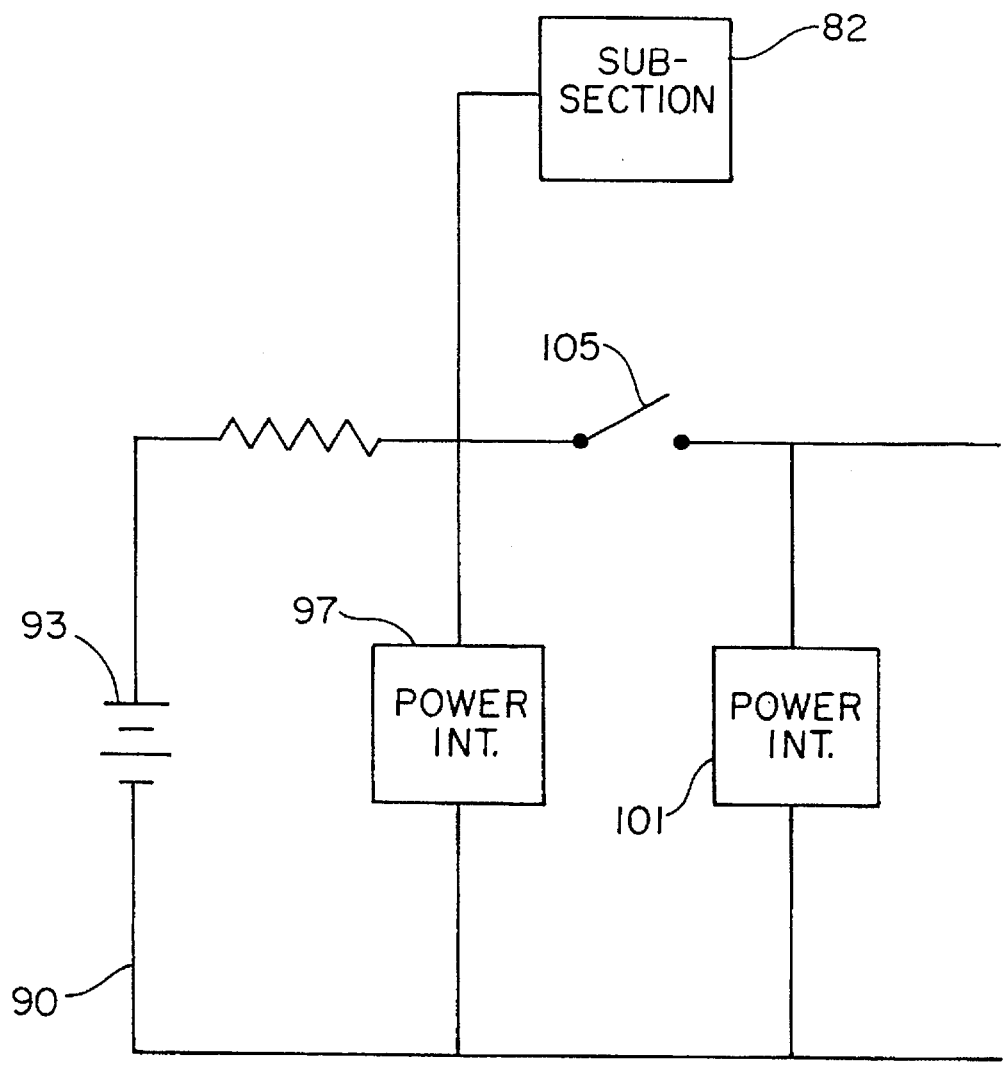
FIG. 6 is a schematic circuit diagram of another embodiment of the implantable cardioverter defibrillator rapid pulse circuitry of this invention.

Another alternate embodiment for charging power intensifying capacitor system 74 after fibrillation is detected is disclosed in FIG. 6. In this embodiment, circuit 90 comprises a relatively low amperage, e.g. milliamps, primary defibrillation battery 93. One example of such a battery 93 comprises a pacing type lithium iodide battery. Other low current, high energy density batteries would include radio-isotope-activated batteries, such as shown in U.S. Pat. Nos.

3,767,947, 4,628,143 and 5,000,579, nuclear batteries, such as shown in U.S. Pat. Nos. 3,094,634, 3,740,273, 4,024,420 and 4,835,433, or thermoelectric batteries, such as shown in U.S. Pat. Nos. 4,002,497 and 4,026,726. Circuit 90 also comprises high power output (approximately 1–3 amperes) intermediate power concentration system 97. A preferred power intensify system 97 would comprise a rechargeable battery, such as lithium titanium di-sulfide battery or other lithium batteries, alkaline batteries, NicCad batteries or lead acid batteries, or a conventional high impedance dual layer capacitor. Power intensifying system 101 comprises a very high amperage (10–30 amps) battery, or a high power, low impedance dual layer capacitor. In operation, circuit 90 allows continuous trickle charge from battery 93 to power concentration system 97. This maintains power concentration system 97 in a substantially fully charged configuration until detection of fibrillation. After detection of fibrillation, power concentration system 97 simultaneously charges the main energy delivery capacitor 32 within sub-section 82 and power intensifying system 101, via switch 105. Capacitor 32 then discharges and is again re-charged with power concentration system 97. However, power concentration system 97 is not normally able to fully charge capacitor 32 in less than at least about 5 seconds. In a closely spaced multiple pulse ICD device power system it is necessary to provide means other than power concentration system 97 to provide charging power for subsequent pulses to the heart. Rather than providing multiple charging pathways or a plurality of capacitors, circuit 90 discloses use of power intensifying system 101 to provide high amperage high power means for charging a main energy delivery capacitor for countershock pulses after the initial countershock/pulse.

The invention also comprises a method for configuring an implantable cardioverter defibrillator main energy delivery electrical circuit for delivery of multiple closely spaced defibrillation pulses to a heart. The method comprises the steps of providing a low power output primary defibrillator battery, and arranging a high power output intermediate power intensifying capacitor system with switch means for permitting the intermediate power intensifying capacitor system to be rechargeable from the primary defibrillator battery and to selectively rapidly charge a main energy delivery capacitor. A main energy delivery capacitor is electrically configured for discharging, in a first pulse, electrical current derived from the primary defibrillator battery and for discharging certain subsequent pulses of electrical current derived from the intermediate power intensifying capacitor system so that the circuit permits the implantable cardioverter defibrillator device to deliver multiple closely spaced defibrillation pulses to a heart using a single capacitor. A further step comprises simultaneously charging both the high power output intermediate power intensifying battery and the main energy delivery capacitor using the low power output primary defibrillator battery.

The embodiment of circuits 67 and 90 are each also advantageous as a rapid pulse power system for use with implantable cardioverter devices. This rapid pulse power system may be integrated into other known or proprietary circuits as a means of enabling rapid and optional transition from a widely spaced defibrillation pulse sequence to a closely spaced defibrillation pulse sequence. This is accomplished without adding any additional main energy delivery capacitors, which would detract from the size and volume advantages of the invention. Accordingly, the invention also discloses a method of configuring an implantable cardioverter defibrillator electrical circuit as a rapid pulse power system to enable rapid transition from a widely spaced defibrillation pulse sequence to a closely spaced defibrillation pulse sequence. the method comprises the steps of providing a low power output primary defibrillator battery, arranging a high power output intermediate power intensifying capacitor system, providing switch means for permitting the intermediate power intensifying capacitor system to rapidly charge a main energy delivery capacitor, responding to a remote signal and selectively discharging a main energy delivery capacitor. The main energy delivery capacitor is discharged, in a first pulse, with an electrical charge derived from the primary defibrillator battery and, in certain subsequent multiple closely spaced defibrillation pulses, with electrical charge derived from the intermediate power intensifying capacitor system. The pulses are deliverable to a heart at any time interval following an initial defibrillation attempt using another defibrillator pulse power source.

We claim:

1. A main energy delivery electrical circuit for use in an implantable cardioverter defibrillator device, comprising:
   a) a low power output primary defibrillator battery;
   b) a high power output intermediate power intensifying capacitor system;
   c) switch means, electrically connected to the intensifying capacitor system and the primary defibrillator battery, for selectively switching between the primary defibrillator battery and the intensifying capacitor system;
   d) a high voltage transformer system electrically connected to the switch means; and
   a main energy delivery capacitor system connected to the transformer system for storing, in a first pulse to be discharged, an electrical charge from the primary defibrillator battery and for storing, as at least one subsequent pulse to be discharged, an electrical charge derived from the intensifying capacitor system,
   such that the electrical circuit permits the implantable cardioverter defibrillator device to deliver multiple closely spaced defibrillation pulses to a heart.

2. The electrical circuit of claim 1 wherein the switch means allows for simultaneous charging from the primary defibrillator battery to both the intensifying capacitor system and the delivery capacitor system.

3. The electrical circuit of claim 1 in which the primary defibrillator battery has a maximum current output of about 3 amperes.

4. The electrical circuit of claim 1 further comprising a control system which uses the switch means to selectively recharge the intensifying capacitor system from the primary defibrillator battery.

5. The electrical circuit of claim 4 in which the intensifying capacitor system has a maximum current output within a range of between 10 amperes and 30 amperes.

6. The electrical circuit of claim 1 in which the delivery capacitor system is charged at a charging rate of between 10 joules per second and 100 joules per second.

7. The electrical circuit of claim 1 further comprising a control system which uses the switch means to selectively switch between the primary defibrillation battery and the intensifying capacitor system to provide energy to the delivery capacitor system such that the delivery capacitor is repeatably able to charge and then discharge in a time interval which is less than 5 seconds between pulses.

8. The electrical circuit of claim 7 in which the time interval is within a range of greater than 10 milliseconds and less than 1 second.

9. A method for configuring an implantable cardioverter defibrillator main energy delivery electrical circuit for delivery of multiple closely spaced defibrillation pulses to a heart comprising the steps of:

a) providing a low power output primary defibrillator battery;
b) providing a high power output intermediate power intensifying capacitor system;
c) periodically recharging the intensifying capacitor system from the primary defibrillator battery;
d) providing a main energy delivery capacitor system;
e) charging the delivery capacitor system with electrical energy derived from the primary defibrillator battery as a first pulse of electrical charge;
f) discharging the first pulse of electrical charge as a defibrillation pulse;
g) subsequently recharging the delivery capacitor system at least once within 5 seconds with electrical energy derived from the intensifying capacitor system as at least one subsequent pulse of electrical charge; and
h) discharging the subsequent pulse of electrical charge.

10. The method of claim 9 further comprising the step of simultaneously charging both the intermediate power intensifying capacitor system and the delivery capacitor system using the primary defibrillator battery.

11. A main energy delivery electrical circuit for use in an implantable cardioverter defibrillator device, comprising:

a) a primary power source having a given electrical power transfer rate;
b) a power intensifying system separate from the primary power source for increasing the electrical power transfer rate above that of the primary power source;
c) switch means, electrically connected to the power intensifying system and the primary power source, for selectively switching between the power intensifying system and the primary power source;
d) a high voltage transformer system electrically connected to the switch means; and
e) a main energy delivery capacitor system connected to the transformer system for storing, in a first pulse to be discharged, an electrical charge from the primary defibrillator battery and for storing, as at least one subsequent pulse to be discharged, an electrical charge derived from the intensifying capacitor system, such that the electrical circuit permits the implantable cardioverter defibrillator device to deliver multiple closely spaced defibrillation pulses to a heart.

12. The electrical circuit of claim 11 in which the primary power source is a battery selected from the set consisting of: a lithium iodide battery, a radioisotope-activated battery, a nuclear battery, or a thermoelectric battery.

13. The electrical circuit of claim 11 in which the power intensifying system is selected from the set consisting of: a lithium battery, a lithium titanium battery, a di-sulfide battery, an alkaline battery, a NiCad battery, a lead acid battery, or a dual layer capacitor.

14. The electrical circuit of claim 11 in which the primary power source has a maximum current of about 3 amperes.

15. The electrical circuit of claim 11 in which the power intensifying system is periodically recharged from the primary power source.

16. The electrical circuit of claim 11 in which the power intensifying system has a maximum current output in a range between about 10 amperes and 30 amperes.

17. The electrical circuit of claim 11 further comprising a control system which uses the switch means to selectively switch between the primary power source and the power intensifying system to provide energy to the delivery capacitor system such that the delivery capacitor is charged in a time interval which is within a range of greater than 10 milliseconds and less than 1 second between pulses.

18. The electrical circuit of claim 11 in which the delivery capacitor system is charged at a charging rate of between 10 joules per second and 100 joules per second.

\* \* \* \* \*